(12) United States Patent
Moss et al.

(10) Patent No.: US 8,401,686 B2
(45) Date of Patent: Mar. 19, 2013

(54) REDUCED REGISTRATION BONDING TEMPLATE

(75) Inventors: Jon Moss, Antioch, CA (US); Rok Sribar, Auburn, CA (US)

(73) Assignee: Align Technology, Inc., San Jose, CA (US)

( * ) Notice: Subject to any disclaimer, the term of this patent is extended or adjusted under 35 U.S.C. 154(b) by 296 days.

(21) Appl. No.: 12/338,307

(22) Filed: Dec. 18, 2008

(65) Prior Publication Data

US 2010/0159412 A1 Jun. 24, 2010

(51) Int. Cl.
*G06F 19/00* (2011.01)

(52) U.S. Cl. ............... 700/98; 700/118; 433/24; 433/72

(58) Field of Classification Search .................... 700/95, 700/98, 118; 433/72, 24
See application file for complete search history.

(56) References Cited

U.S. PATENT DOCUMENTS

| | | |
|---|---|---|
| 2,467,432 A | 4/1949 | Kesling |
| 3,407,500 A | 10/1968 | Kesling |
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |

(Continued)

FOREIGN PATENT DOCUMENTS

| | | |
|---|---|---|
| AU | 3031677 A | 5/1979 |
| AU | 517102 B2 | 7/1981 |

(Continued)

OTHER PUBLICATIONS

AADR, American Association for Dental Research, Summary of Activities, Mar. 20-23, 1980, Los ngeles, CA, p. 195.

(Continued)

*Primary Examiner* — Mohammad Ali
*Assistant Examiner* — Anthony Whittington
(74) *Attorney, Agent, or Firm* — Wilson Sonsini Goodrich & Rosati

(57) ABSTRACT

A dental template for positioning an object on teeth of a patient and method for fabricating the same. The method includes creating a digital model of the patient's teeth, creating a simplified template model based on the digital model, and fabricating the dental template based on the simplified template model. The template model is simplified by removing certain features of the patient's tooth anatomy. The dental template can be located on a patient's teeth using four or fewer positioning teeth.

14 Claims, 5 Drawing Sheets

U.S. PATENT DOCUMENTS

| | | | |
|---|---|---|---|
| 4,575,805 A | 3/1986 | Moermann et al. | |
| 4,591,341 A | 5/1986 | Andrews | |
| 4,609,349 A | 9/1986 | Cain | |
| 4,611,288 A | 9/1986 | Duret et al. | |
| 4,656,860 A | 4/1987 | Orthuber et al. | |
| 4,663,720 A | 5/1987 | Duret et al. | |
| 4,664,626 A | 5/1987 | Kesling | |
| 4,676,747 A | 6/1987 | Kesling | |
| 4,742,464 A | 5/1988 | Duret et al. | |
| 4,755,139 A | 7/1988 | Abbatte et al. | |
| 4,763,791 A | 8/1988 | Halverson et al. | |
| 4,793,803 A | 12/1988 | Martz | |
| 4,798,534 A | 1/1989 | Breads | |
| 4,836,778 A | 6/1989 | Baumrind et al. | |
| 4,837,732 A | 6/1989 | Brandestini et al. | |
| 4,850,864 A | 7/1989 | Diamond | |
| 4,850,865 A | 7/1989 | Napolitano | |
| 4,856,991 A | 8/1989 | Breads et al. | |
| 4,877,398 A | 10/1989 | Kesling | |
| 4,880,380 A | 11/1989 | Martz | |
| 4,889,238 A | 12/1989 | Batchelor | |
| 4,890,608 A | 1/1990 | Steer | |
| 4,935,635 A | 6/1990 | O'Harra | |
| 4,936,862 A | 6/1990 | Walker et al. | |
| 4,937,928 A | 7/1990 | van der Zel | |
| 4,941,826 A | 7/1990 | Loran et al. | |
| 4,964,770 A | 10/1990 | Steinbichler et al. | |
| 4,975,052 A | 12/1990 | Spencer et al. | |
| 4,983,334 A | 1/1991 | Adell | |
| 5,011,405 A | 4/1991 | Lemchen | |
| 5,017,133 A | 5/1991 | Miura | |
| 5,027,281 A | 6/1991 | Rekow et al. | |
| 5,035,613 A | 7/1991 | Breads et al. | |
| 5,055,039 A | 10/1991 | Abbatte et al. | |
| 5,059,118 A | 10/1991 | Breads et al. | |
| 5,100,316 A | 3/1992 | Wildman | |
| 5,121,333 A | 6/1992 | Riley et al. | |
| 5,125,832 A | 6/1992 | Kesling | |
| 5,128,870 A | 7/1992 | Erdman et al. | |
| 5,130,064 A | 7/1992 | Smalley | |
| 5,131,843 A | 7/1992 | Hilgers et al. | |
| 5,131,844 A | 7/1992 | Marinaccio et al. | |
| 5,139,419 A | 8/1992 | Andreiko et al. | |
| 5,145,364 A | 9/1992 | Martz et al. | |
| 5,176,517 A | 1/1993 | Truax | |
| 5,184,306 A | 2/1993 | Erdman et al. | |
| 5,186,623 A | 2/1993 | Breads et al. | |
| 5,257,203 A | 10/1993 | Riley et al. | |
| 5,273,429 A | 12/1993 | Rekow et al. | |
| 5,278,756 A | 1/1994 | Lemchen et al. | |
| 5,328,362 A | 7/1994 | Watson et al. | |
| 5,338,198 A | 8/1994 | Wu et al. | |
| 5,340,309 A | 8/1994 | Robertson | |
| 5,342,202 A | 8/1994 | Deshayes | |
| 5,368,478 A | 11/1994 | Andreiko et al. | |
| 5,382,164 A | 1/1995 | Stern | |
| 5,395,238 A | 3/1995 | Andreiko et al. | |
| 5,431,562 A | 7/1995 | Andreiko et al. | |
| 5,440,326 A | 8/1995 | Quinn | |
| 5,440,496 A | 8/1995 | Andersson et al. | |
| 5,447,432 A | 9/1995 | Andreiko et al. | |
| 5,452,219 A | 9/1995 | Dehoff et al. | |
| 5,454,717 A | 10/1995 | Andreiko et al. | |
| 5,456,600 A | 10/1995 | Andreiko et al. | |
| 5,474,448 A | 12/1995 | Andreiko et al. | |
| RE35,169 E | 3/1996 | Lemchen et al. | |
| 5,518,397 A | 5/1996 | Andreiko et al. | |
| 5,528,735 A | 6/1996 | Strasnick et al. | |
| 5,533,895 A | 7/1996 | Andreiko et al. | |
| 5,542,842 A | 8/1996 | Andreiko et al. | |
| 5,549,476 A | 8/1996 | Stern | |
| 5,562,448 A | 10/1996 | Mushabac | |
| 5,587,912 A | 12/1996 | Andersson et al. | |
| 5,605,459 A | 2/1997 | Kuroda et al. | |
| 5,607,305 A | 3/1997 | Andersson et al. | |
| 5,614,075 A | 3/1997 | Andre | |
| 5,621,648 A | 4/1997 | Crump | |
| 5,645,420 A | 7/1997 | Bergersen | |
| 5,645,421 A | 7/1997 | Slootsky | |
| 5,655,653 A | 8/1997 | Chester | |
| 5,683,243 A | 11/1997 | Andreiko et al. | |
| 5,692,894 A | 12/1997 | Schwartz et al. | |
| 5,725,376 A | 3/1998 | Poirier | |
| 5,725,378 A | 3/1998 | Wang | |
| 5,733,126 A | 3/1998 | Andersson et al. | |
| 5,740,267 A | 4/1998 | Echerer et al. | |
| 5,742,700 A | 4/1998 | Yoon et al. | |
| 5,799,100 A | 8/1998 | Clarke et al. | |
| 5,800,174 A | 9/1998 | Andersson | |
| 5,823,778 A | 10/1998 | Schmitt et al. | |
| 5,848,115 A | 12/1998 | Little et al. | |
| 5,857,853 A | 1/1999 | van Nifterick et al. | |
| 5,866,058 A | 2/1999 | Batchelder et al. | |
| 5,879,158 A | 3/1999 | Doyle et al. | |
| 5,880,961 A | 3/1999 | Crump | |
| 5,880,962 A | 3/1999 | Andersson et al. | |
| 5,934,288 A | 8/1999 | Avila et al. | |
| 5,957,686 A | 9/1999 | Anthony | |
| 5,964,587 A | 10/1999 | Sato | |
| 5,971,754 A | 10/1999 | Sondhi et al. | |
| 5,975,893 A | 11/1999 | Chishti et al. | |
| 6,015,289 A | 1/2000 | Andreiko et al. | |
| 6,044,309 A | 3/2000 | Honda | |
| 6,049,743 A | 4/2000 | Baba | |
| 6,062,861 A | 5/2000 | Andersson | |
| 6,068,482 A | 5/2000 | Snow | |
| 6,099,314 A | 8/2000 | Kopelman et al. | |
| 6,123,544 A | 9/2000 | Cleary | |
| 6,152,731 A | 11/2000 | Jordan et al. | |
| 6,174,168 B1 * | 1/2001 | Dehoff et al. | 433/202.1 |
| 6,183,248 B1 | 2/2001 | Chishti et al. | |
| 6,190,165 B1 | 2/2001 | Andreiko et al. | |
| 6,217,325 B1 | 4/2001 | Chishti et al. | |
| 6,217,334 B1 | 4/2001 | Hultgren | |
| 6,244,861 B1 | 6/2001 | Andreiko et al. | |
| 6,283,753 B1 * | 9/2001 | Willoughby | 433/172 |
| 6,309,215 B1 | 10/2001 | Phan et al. | |
| 6,315,553 B1 | 11/2001 | Sachdeva et al. | |
| 6,322,359 B1 | 11/2001 | Jordan et al. | |
| 6,350,120 B1 | 2/2002 | Sachdeva et al. | |
| 6,382,975 B1 | 5/2002 | Poirier | |
| 6,398,548 B1 | 6/2002 | Muhammad et al. | |
| 6,402,707 B1 | 6/2002 | Ernst | |
| 6,482,298 B1 | 11/2002 | Bhatnagar | |
| 6,488,503 B1 * | 12/2002 | Lichkus et al. | 433/202.1 |
| 6,524,101 B1 | 2/2003 | Phan et al. | |
| 6,554,611 B2 | 4/2003 | Chishti et al. | |
| 6,572,372 B1 | 6/2003 | Phan et al. | |
| 6,629,840 B2 | 10/2003 | Chishti et al. | |
| 6,705,863 B2 | 3/2004 | Phan et al. | |
| 6,722,880 B2 | 4/2004 | Chishti et al. | |
| 7,056,115 B2 * | 6/2006 | Phan et al. | 433/24 |
| 7,442,040 B2 * | 10/2008 | Kuo | 433/202.1 |
| 7,476,100 B2 * | 1/2009 | Kuo | 433/6 |
| 7,600,999 B2 * | 10/2009 | Knopp | 433/24 |
| 7,658,610 B2 * | 2/2010 | Knopp | 433/24 |
| 2002/0006597 A1 | 1/2002 | Andreiko et al. | |
| 2003/0009252 A1 | 1/2003 | Pavlovskaia et al. | |
| 2003/0139834 A1 | 7/2003 | Nikolskiy et al. | |
| 2003/0162147 A1 * | 8/2003 | Dequeker | 433/167 |
| 2003/0222366 A1 * | 12/2003 | Stangel et al. | 264/16 |
| 2003/0224311 A1 | 12/2003 | Cronauer | |
| 2004/0128010 A1 | 7/2004 | Pavlovskaia et al. | |
| 2004/0229185 A1 * | 11/2004 | Knopp | 433/24 |
| 2004/0253562 A1 * | 12/2004 | Knopp | 433/24 |
| 2005/0042569 A1 * | 2/2005 | Phan et al. | 433/24 |
| 2005/0055118 A1 | 3/2005 | Nikolskiy et al. | |
| 2005/0064360 A1 * | 3/2005 | Wen et al. | 433/24 |
| 2005/0070782 A1 * | 3/2005 | Brodkin | 600/407 |
| 2006/0084030 A1 * | 4/2006 | Phan et al. | 433/72 |
| 2006/0154207 A1 * | 7/2006 | Kuo | 433/202.1 |
| 2006/0257817 A1 * | 11/2006 | Shelton | 433/75 |
| 2007/0009855 A1 * | 1/2007 | Stonisch | 433/215 |
| 2008/0064005 A1 * | 3/2008 | Meitner | 433/74 |
| 2008/0096152 A1 * | 4/2008 | Cheang | 433/24 |
| 2008/0160485 A1 * | 7/2008 | Touchstone | 433/215 |
| 2008/0166681 A1 * | 7/2008 | Weinstein et al. | 433/76 |

| | | | |
|---|---|---|---|
| 2008/0176189 | A1* | 7/2008 | Stonisch .................. 433/215 |
| 2010/0159412 | A1* | 6/2010 | Moss et al. ................ 433/24 |
| 2010/0159413 | A1* | 6/2010 | Kuo .......................... 433/24 |

FOREIGN PATENT DOCUMENTS

| | | |
|---|---|---|
| AU | 5598894 A | 6/1994 |
| CA | 1121955 | 4/1982 |
| DE | 2749802 | 5/1978 |
| DE | 69327661 T | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 8/1995 |
| EP | 0731673 B1 | 9/1996 |
| EP | 0774933 B1 | 5/1997 |
| ES | 463897 | 1/1980 |
| FR | 2369828 A1 | 6/1978 |
| FR | 2652256 A1 | 3/1991 |
| GB | 15500777 | 8/1979 |
| JP | 53-058191 | 5/1978 |
| JP | 04-028359 | 1/1992 |
| JP | 08-508174 | 9/1996 |
| WO | WO 90/08512 A1 | 8/1990 |
| WO | WO 91/04713 A1 | 4/1991 |
| WO | WO 94/10935 A1 | 5/1994 |
| WO | WO 98/32394 A1 | 7/1998 |
| WO | WO 98/44865 A1 | 10/1998 |
| WO | WO 98/58596 A1 | 12/1998 |

OTHER PUBLICATIONS

Alcaniz, et aL, "An Advanced System for the Simulation and Planning of Orthodontic Treatments," Karl HF Heinz Holme and Ron Kikinis (eds.), Visualization in Biomedical Computing, 4th Intl. Conf., VBC '96, Hamburg, Germany, Sep. 22-25, 1996, Springer-Verlag, pp. 511-520.
Alexander et al., "The DigiGraph Work Station Part 2 Clinical Management," JCO, pp. 402-407 (Jul. 1990).
Altschuler et al., "Analysis of 3-D Data for Comparative 3-D Serial Growth Pattern Studies of Oral-Facial Structures," AADR Abstracts, Program and Abstracts of Papers, 57th General Session, IADR HP Annual Session, Mar. 29, 1979-Apr. 1, 1979, New Orleans Marriot, Journal of Dental Research, vol. 58, Jan. 1979, Special Issue A, p. 221.
Altschuler et al., "Laser Electro-Optic System for Rapid Three-Dimensional (3D) Topographic Mapping of Surfaces," Optical Engineering, 20(6):953-961 (1981).
Altschuler et al., "Measuring Surfaces Space-Coded by a Laser-Projected Dot Matrix," SPIE Imaging q Applications for Automated Industrial Inspection and Assembly, vol. 182, p. 187-191 (1979).
Altschuler, "3D Mapping of Maxillo-Facial Prosthesis," AADR Abstract #607, 2 pages total, (1980).
Andersson et al., "Clinical Results with Titanium Crowns Fabricated with Machine Duplication and Spark Erosion," Acta. Odontol. Scand., 47:279-286 (1989).
Andrews, The Six Keys to Optimal Occlusion Straight Wire, Chapter 3, pp. 13-24 (No Date Given).
Bartels, et al., An Introduction to Splines for Use in Computer Graphics and Geometric Modeling, Morgan Kaufmann Publishers, pp. 422-425 (1987).
Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.
Baumrind et al., "Mapping the Skull in 3-D," reprinted from J. Calif. Dent. Assoc., 48(2), 11 pages total, (1972 Fall Issue).
Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of III., Aug. 26-30, 1975, pp. 142-166.
Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).
Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff et al., "Computerized Analysis of Occlusion in the Postcanine Dentition," Am. J. Orthod., 61(3): 245-254 (Mar. 1972).
Biggerstaff, "Computerized Diagnostic Setups and Simulations," Angle Orthod., 40(1):28-36 (Jan. 1970).
Biostar Opeation & Training Manual. Great Lakes Orthodontics, Ltd. 199 Fire Tower Drive,Tonawanda, New York. 14150-5890, 20 pages total (No Date Given).
Blu, et al., "Linear interpolation revitalized", IEEE Trans. Image Proc., 13(5):710-719 (May 2004.
Bourke, "Coordinate System Transformation," (Jun. 1996), p. 1, retrieved from the Internet Nov. 5, 2004, URL <http://astronomy.swin.edu.au/—pbourke/prolection/coords>.
Boyd et al., "Three Dimensional Diagnosis and Orthodontic Treatment of Complex Malocclusions With the Invisalipn Appliance," Semin. Orthod., 7(4):274-293 (Dec. 2001).
Brandestini et al., "Computer Machined Ceramic Inlays: In Vitro Marginal Adaptation," J. Dent. Res.Special Issue, Abstracts, vol. 64, p. 208 (1985).
Brook et al., "An Image Analysis System for the Determination of Tooth Dimensions from Study Casts: IK Comparison with Manual Measurements of Mesio-distal Diameter," J. Dent. Res., 65(3):428-431 (Mar. 1986.
Burstone (interview), "Dr. Charles J. Burstone on the Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979.
Burstone et al., Precision Adjustment of the Transpalatal Lingual Arch: Computer Arch Form IN Predetermination, Am, Journal of Orthodontics, vol. 79, No. 2 (Feb. 1981), pp. 115-133.
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1: CAD/CAM: The Computer Moves Chairside," "Part 2: F. Duret—A Man With a Vision," "Part 3: The Computer Gives New Vision—Literally," "Part 4: Bytes 'N Bites" The Computer Moves From the Front Desk to the Operatory, Canadian Dental Journal, vol. 54(9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Cranio facial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).

DCS Dental AG, "The CAD/CAM 'DCS Titan System' for Production of Crowns/Bridges," DSC ProductionAG, pp. 1-7 (Jan. 1992.

Definition for gingiva. Dictionary.com p. 1-3. Retrieved from the internet Nov. 5, 2004 <http://reference.com/search/search?q=gingiva>.

DeFranco et al., "Three-Dimensional Large Displacement Analysis of Orthodontic Appliances," J. Biomechanics, 9:793-801 (1976).

Dental Institute University of Zurich Switzerland, Program for International Symposium JD on Computer Restorations: State of the Art of the CEREC-Method, May 1991, 2 pages total.

Dentrac Corporation, Dentrac document, pp. 4-13 (No Date Given).

Dent-X posted on Sep. 24, 1998 at <http://www.dent-x.com/DentSim.htm>, 6 pages.

Doyle, "Digital Dentistry," Computer Graphics World, pp. 50-52, 54 (Oct. 2000.

DuraClearTM product information, Allesee Orthodontic Appliances-Pro Lab, 1 page (No Date Given).

Duret et al, "CAD-CAM in Dentistry," J. Am. Dent. Assoc. 117:715-720 (Nov. 1988.

Duret et al., "CAD/CAM Imaging in Dentistry," Curr. Opin. Dent., 1:150-154 (1991.

Duret, "The Dental CAD/CAM, General Description of the Project," Henson International Product Brochure, 18 pages total, Jan. 1986.

Duret,"Vers Une Prosthese Informatisee," (English translation attached), Tonus, vol. 75, pp. 55-57 (Nov. 15, 1985).

Economides, "The Microcomputer in the Orthodontic Office," JCO, pp. 767-772 (Nov. 1979.

Elsasser, Some Observations on the History and Uses of the Kesling Positioner, Am. J. Orthod. (1950) 36:368-374.

English translation of Japanese Laid-Open Publication No. 63-11148 to inventor T. Ozukuri (Laid-Open on Jan. 18, 1998) pp. 1-7.

Felton et al., "A Computerized Analysis of the Shape and Stability of Mandibular Arch Form," Am. J. Orthod. Dentofacial Orthop., 92(6):478-483 (Dec. 1987.

Friede et al., "Accuracy of Cephalometric Prediction in Orthognathic Surgery," Abstract of Papers, J. Dent. Res., 70:754-760 (1987.

Futterling et a/., "Automated Finite Element Modeling of a Human Mandible with Dental Implants," JS WSCG '98 —Conference Program, retrieved from the Internet: <http://wscg.zcu.cz/wscg98/papers98/Strasser 98.pdf>, 8 pages.

Gao et al., "3-D element Generation for Multi-Connected Complex Dental and Mandibular Structure," Proc. Intl Workshop on Medical Imaging and Augmented Reality, pp. 267-271 (Jun. 12, 2001.

Gim-Alldent Deutschland, "Das DUX System: Die Technik," 2 pages total (No Date Given.

Gottlieb et al., "JCO Interviews Dr. James A. McNamura, Jr., on the Frankel Appliance: Part 2: Clinical 1-1 Management," J. Clin. Orthod., 16(6):390-407 (Jun. 1982.

Grayson, "New Methods for Three Dimensional Analysis of Craniofacial Deformity, Symposium:JW Computerized Facial Imaging in Oral and Maxiiofacial Surgery," AAOMS, 3 pages total, (Sep. 13, 1990).

Guess et al., "Computer Treatment Estimates in Orthodontics and Orthognathic Surgery," JCO, pp. 262-28 (Apr. 1989).

Heaven et a/., "Computer-Based Image Analysis of Artificial Root Surface Caries," Abstracts of Papers, J. Dent. Res., 70:528 (Apr. 17-21, 1991).

Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingamp-production/november011996/simulatingstressputonfa...>.

Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total.

Hoffmann, et al., "Role of Cephalometry for Planning of Jaw Orthopedics and Jaw Surgery Procedures," 0 (Article Summary in English, article in German), Informathnen, pp. 375-396 (Mar. 1991.

Hojjatie et al., "Three-Dimensional Finite Element Analysis of Glass-Ceramic Dental Crowns," J. Biomech., 23(11):1157-1166 (1990.

Huckins, "CAD-CAM Generated Mandibular Model Prototype from MRI Data," AAOMS, p. 96 (1999.

Important Tip About Wearing the Red White & Blue Active Clear Retainer System, Allesee Orthodontic Appliances-Pro Lab, 1 page 1998).

Inside the ADA, JADA, 118:286-294 (Mar. 1989).

JCO Interviews, Craig Andreiko , DDS, MS on the Elan and Orthos Systems, JCO, pp. 459-468 (Aug. 1994).

JCO Interviews, Dr. Homer W. Phillips on Computers in Orthodontic Practice, Part 2, JCO, pp. 819-831.

Jerrold, "The Problem, Electronic Data Transmission and the Law," AJO-DO, pp. 478-479 (Apr. 1988.

Jones et al., "An Assessment of the Fit of a Parabolic Curve to Pre- and Post-Treatment Dental Arches," Br. J. Orthod., 16:85-93 (1989).

JP Faber et al., "Computerized Interactive Orthodontic Treatment Planning," Am. J. Orthod., 73(1)36-46. Jan. 1978.

Kamada et.al., Construction of Tooth Positioners with LTV Vinyl Silicone Rubber and Some Case KJ Reports, J. Nihon University School of Dentistry (1982) 24(1):1-27.

Kanazawa et al., "Three-Dimensional Measurements of the Occlusal Surfaces of Upper Molars in a Dutch Population," J. Dent Res., 63(11):1298-1301 (Nov. 1984).

Kesling et al., The Philosophy of the Tooth Positioning Appliance, American Journal of Orthodontics and Oral surgery. 1945; 31:297-304.

Kesling, Coordinating the Predetermined Pattern and Tooth Positioner with Conventional Treatment, KN Am. J. Orthod. Oral Surg. (1946) 32:285-293.

Ki Kamada et.al., Case Reports on Tooth Positioners Using LTV Vinyl Silicone Rubber, J. Nihon University School of Dentistry (1984) 26(1): 11-29.

Kleeman et al., The Speed Positioner, J. Clin. Orthod. (1996) 30:673-680.

Kochanek, "Interpolating Splines with Local Tension, Continuity and Bias Control," Computer Graphics, ri 18(3):33-41 (Jul. 1984).

KM Oral Surgery (1945) 31 :297-30.

Kunii et al., "Articulation Simulation for an Intelligent Dental Care System," Displays 15:181-188 (1994).

Kuroda et al., Three-Dimensional Dental Cast Analyzing System Using Laser Scanning, Am. J. Orthod. Dentofac. Orthop. (1996) 110:365-369.

Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991).

Leinfelder, et al., "A New Method for Generating Ceramic Restorations: a CAD-CAM System," J. Am. 1-1 Dent. Assoc., 118(6):703-707 (Jun. 1989.

Manetti, et al., "Computer-Aided Cefalometry and New Mechanics in Orthodontics," (Article Summary in English, article in German), Fortschr Kieferorthop. 44, 370-376 (Nr. 5), 1983.

McCann, "Inside the ADA," J. Amer. Dent. Assoc., 118:286-294 (Mar. 1989.

McNamara et al., "Invisible Retainers," J. Cfin. Orthod., pp. 570-578 (Aug. 1985).

McNamara et al., Orthodontic and Orthopedic Treatment in the Mixed Dentition, Needham Press, pp. 347-353 (Jan. 1993).

Moermann et al., "Computer Machined Adhesive Porcelain Inlays: Margin Adaptation after Fatigue Stress," IADR Abstract 339, J. Dent. Res., 66(a):763 (1987).

Moles, "Correcting Mild Malalignments—As Easy As One, Two, Three," AOA/Pro Corner, vol. 11, No. 1, 2 pages (2002).

Mormann et al., "Marginale Adaptation von adhasuven Porzellaninlays in vitro," Separatdruck aus:Schweiz. Mschr. Zahnmed. 95: 1118-1129, 1985.

Nahoum, "The Vacuum Formed Dental Contour Appliance," N. Y. State Dent. J., 30(9):385-390 (Nov. 1964).

Nash, "CEREC CAD/CAM Inlays: Aesthetics and Durability in a Single Appointment," Dent. Today, 9(8):20, 22-23 (Oct. 1990).

Nishiyama et al., "A New Construction of Tooth Repositioner by LTV Vinyl Silicone Rubber," J. Nihon Univ. Sch. Dent., 19(2):93-102 (1977).

Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.

Pinkham, "Foolish Concept Propels Technology," Dentist, 3 pages total, Jan./Feb. 1989.

Pinkham, "Inventor's CAD/CAM May Transform Dentistry," Dentist, 3 pages total, Sep. 1990.

Ponitz, "Invisible Retainers," Am. J. Orthod., 59(3):266-272 (Mar. 1971).

Procera Research Projects, "Procera Research Projects 1993—Abstract Collection," pp. 3-7 28 (1993.

Proffit et al., Contemporary Orthodontics, (Second Ed.), Chapter 15, Mosby Inc., pp. 470-533 Oct. 1993.

Raintree Essix & ARS Materials, Inc., Raintree Essix, Technical Magazine Table of contents and q Essix Appliances, <http://www.essix.com/magazine/defaulthtml> Aug. 13, 1997.

Redmond et al., "Clinical Implications of Digital Orthodontics," Am. J. Orthod. Dentofacial Orthop.,117(2):240-242 (2000.

Rekow et a/., "CAD/CAM for Dental Restorations—Some of the Curious Challenges," IEEE Trans. Biomed. Eng., 38(4)344-345 (Apr. 1991.

Rekow et al., "Comparison of Three Data Acquisition Techniques for 3-D Tooth Surface Mapping," LM Annual International Conference of the IEEE Engineering in Medicine and Biology Society, 13(1):344-345 1991.

Rekow, "A Review of the Developments in Dental CAD/CAM Systems," (contains references toLN Japanese efforts and content of the papers of particular interest to the clinician are indicated with a one line summary of their content in the bibliography), Curr. Opin. Dent., 2:25-33 (Jun. 1992.

Rekow, "CAD/CAM in Dentistry: A Historical Perspective and View of the Future," J. Can. Dent. Assoc., 58(4):283, 287-288 (Apr. 1992.

Rekow, "Computer-Aided Design and Manufacturing in Dentistry: A Review of the State of the Art," J. Prosthet. Dent., 58(4):512-516 (Oct. 1987.

Rekow, "Dental CAD-CAM Systems: What is the State of the Art?", J. Amer. Dent. Assoc., 122:43-48 1991.

Rekow, "Feasibility of an Automated System for Production of Dental Restorations, Ph.D. Thesis," Univ. of Minnesota, 244 pages total, Nov. 1988.

Richmond et al., "The Development of a 3D Cast Analysis System," Br. J. Orthod., 13(1):53-54 (Jan. 1986).

Richmond et al., "The Development of the PAR Index (Peer Assessment Rating): Reliability and Validity," Eur. J. Orthod., 14:125-139 (1992).

Richmond, "Recording the Dental Cast in Three Dimensions," Am. J. Orthod. Dentofacial Orthop., 92(3):199-206 (Sep. 1987).

Rudge, "Dental Arch Analysis: Arch Form, A Review of the Literature," Eur. J. Orthod., 3(4):279-284 1981.

Sakuda et al., "Integrated Information-Processing System in Clinical Orthodontics: An Approach with Use of a Computer Network System," Am. J. Orthod. Dentofacial Orthop., 101(3): 210-220 (Mar. 1992).

Schellhas et al., "Three-Dimensional Computed Tomography in Maxillofacial Surgical Planning," Arch. Otolamp!. Head Neck Sur9., 114:438-442 (Apr. 1988).

Schroeder et al., Eds. The Visual Toolkit, Prentice Hall PTR, New Jersey (1998) Chapters 6, 8 & 9, (pp. 153-210,309-354, and 355-428, respectively.

Shilliday, (1971). Minimizing finishing problems with the mini-positioner, Am. J. Orthod. 59:596-599.

Siemens, "CEREC—Computer-Reconstruction," High Tech in der Zahnmedizin, 14 pages total (No Date Given).

Sinclair, "The Readers' Corner," J. Clin. Orthod., 26(6):369-372 (Jun. 1992.

Sirona Dental Systems GmbH, CEREC 3D, Manuel utiiisateur, Version 2.0X (in French), 2003,114 pages total.

Stoll et al., "Computer-aided Technologies in Dentistry," (article summary in English, article in German), Dtsch Zahna'rztl Z 45, pp. 314-322 (1990).

Sturman, "Interactive Keyframe Animation of 3-D Articulated Models," Proceedings Graphics Interface '84, May-Jun. 1984, pp. 35-40.

The Choice Is Clear: Red, White & Blue . . . The Simple, Affordable, No-Braces Treatment, Allesee HI Orthodontic Appliances-Pro Lab product information for doctors. http://ormco.com/aoa/appliancesservices/RWB/doctorhtml>, 5 pages (May 19, 2003).

The Choice is Clear: Red, White & Blue . . . The Simple, Affordable, No-Braces Treatment, Allesee HJ Orthodontic Appliances-Pro Lab product information for patients, <http://ormco.com/aoa/appliancesservices/RWB/patients.html>, 2 pages (May 19, 2003).

The Choice Is Clear: Red, White & Blue . . . The Simple, Affordable, No-Braces Treatment, Allesee Orthodontic Appliances-Pro Lab product information, 6 pages (2003).

The Red, White & Blue Way to Improve Your Smile! Allesee Orthodontic Appliances-Pro Lab product information for patients, 2 pages 1992.

Truax L., "Truax Clasp-Less(TM) Appliance System," Funct. Orthod., 9(5):22-4, 26-8 (Sep.-Oct. 1992).

Tru-Tain Orthodontic & Dental Supplies, Product Brochure, Rochester, Minnesota 55902, 16 pages total (No Date Given).

U.S. Department of Commerce, National Technical Information Service, "Automated Crown Replication Using Solid Photography SM," Solid Photography Inc., Melville NY, Oct. 1977, 20 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050,342, filed Jun. 20, 1997, 41 pages total.

Van Der Linden et al., "Three-Dimensional Analysis of Dental Casts by Means of the Optocom," J. Dent. Res., p. 1100 (Jul.-Aug. 1972).

Van Der Linden, "A New Method to Determine Tooth Positions and Dental Arch Dimensions," J. Dent. Res., 51(4):1104 (Jul.-Aug. 1972).

Van Der Zel, "Ceramic-Fused-to-Metal Restorations with a New CAD/CAM System," Quintessence Int., 24(11):769-778 (1993.

Varady et al., "Reverse Engineering of Geometric Models—An Introduction," Computer-Aided Design, 29(4):255-268,1997.

Verstreken et al., "An Image-Guided Planning System for Endosseous Oral Implants," IEEE Trans. Med. Imaging, 17(5):842-852 (Oct. 1998.

Warunek et al., Physical and Mechanical Properties of Elastomers in Orthodonic Positioners, Am J. Orthod. Dentofac. Orthop, vol. 95, No. 5, (May 1989) pp. 399-400.

Warunek et.al., Clinical Use of Silicone Elastomer Applicances, JCO (1989) XXIII(10):694-700.

Wells, Application of the Positioner Appliance in Orthodontic Treatment, Am. J. Orthodont. (1970) 58:351-366.

Williams, "Dentistry and CAD/CAM: Another French Revolution," J. Dent. Practice Admin., pp. 2-5 (Jan./Mar. 1987.

Williams, "The Switzerland and Minnesota Developments in CAD/CAM," J. Dent. Practice Admin., pp. 50-55 (Apr./Jun. 1987.

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1999.

WSCG'98—Conference Program, "The Sixth International Conference in Central Europe on Computer Graphics and Visualization '98," Feb. 9-13, 1998, pp. 1-7, retrieved from the Internet on Nov. 5, 2004,URL<http://wscg.zeu.cz/wscg98/wscg98.h>.

Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001.

Yamamoto et al., "Optical Measurement of Dental Cast Profile and Application to Analysis of Three-Dimensional Tooth Movement in Orthodontics," Front. Med. Biol. Eng., 1(2):119-130 (1988).

Yamamoto et al., "Three-Dimensional Measurement of Dental Cast Profiles and Its Applications to Orthodontics," Conf. Proc. IEEE Eng. Med. Biol. Soc., 12(5):2051-2053 (1990).

Yamany et al., "A System for Human Jaw Modeling Using Intra-Oral Images," Proc. of the 20th AnnualConf. of the IEEE Engineering in Medicine and Biology Society, Nov. 1, 1998, vol. 2, pp. 563-566.

Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980.

Yoshii, "Research on a New Orthodontic Appliance: The Dynamic Positioner (D.P.); II. The D.P.Manufacturing Procedure and Clinical Applications," Nippon Dental Review, 454:107-130 (Aug. 1980).

Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980.

Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).

You May Be a Candidate for This Invisible No-Braces Treatment, Allesee Orthodontic Appliances—Pro Lab product information for patients, 2 pages (No Date Given).

\* cited by examiner

REDUCED REGISTRATION BONDING TEMPLATE

BACKGROUND

The present invention relates generally to the field of orthodontics, and more particularly to an apparatus for bonding an orthodontic bracket to a tooth and a method for making the same.

The fundamental objectives in orthodontics are to move a patient's teeth to a position where the mechanical function of the dentition is optimized and to improve the aesthetic appearance of the patient's teeth. The traditional method that orthodontists use is to attach brackets and wires onto the patient's dentition. Once mounted on the teeth, the wires exert continual light forces through the brackets onto the teeth. These forces initiate the body's biological bone remodeling response and the teeth gradually progress toward their desired final positions. During the treatment period, the treatment professional reactively adjusts the wires and bands to provide a new force and move the teeth toward their desired or final destination.

Orthodontic brackets are often bonded directly to the patient's teeth using a small quantity of adhesive placed on the base of each bracket and the bracket is then placed on a selected tooth while the patient is in the dental chair. Once the adhesive has hardened, the bracket is bonded to the tooth with sufficient strength to withstand subsequent orthodontic forces as treatment progresses. One shortcoming with this technique is the difficulty in accessing the optimal position on the tooth surface for bracket placement on severely crowded teeth or in teeth where the bonding surface is obstructed by teeth in the opposing arch during jaw closure. With posterior teeth, the treatment professional may have difficulty seeing the precise position of the bracket relative to the tooth surface due to limited working space. Also, for most bonding agents, it is necessary to minimize moisture contamination from the patient's saliva for adequate bonding strength. This can prolong the procedure and also unduly impair the accuracy of placement of the brackets on the teeth.

One way to overcome some of the limitations of direct bracket placement is with indirect bonding. Typically, a routine impression of each of the patient's upper and lower dental arches is taken and either sent to a lab or used in the office to create a replica plaster model of each impression after the patient has left the office. Brackets are bonded to the sealed plaster models using a temporary adhesive. A transfer tray is then made by placing matrix material, usually consisting of silicone rubber, over both the model and brackets. The matrix material then assumes a configuration that matches the shape of the replica teeth of the plaster model with the brackets in the desired position. The matrix material then polymerizes and hardens to form a tray. The temporary adhesive is removed, and permanent adhesive is placed on the base of each bracket in the tray, which is then placed over matching portions of the patient's dental arches. Since the configuration of the interior surface of the tray closely matches the respective portions of the patient's dental arches, each bracket location is transferred onto the patient's teeth at precisely the same location that corresponds to the previous location of the same bracket on the plaster model. The adhesive is hardened and the matrix removed, leaving the brackets in the desired positions. This indirect method, however, is labor intensive and fabrication of the intricate details (corresponding to the details of the patient's teeth) of the tray is complex and time-consuming.

SUMMARY

In accordance with one embodiment, a method is provided for fabricating a dental template configured to position an object on teeth of a patient. A digital model of the patient's teeth is created. A template model is then created. The template model includes teeth based on the digital model. Some teeth on the template model include a substantially planar occlusal portion. A dental template is then fabricated using the template model.

DESCRIPTION

Embodiments of a simplified dental template are disclosed to support positioning an object on a patient's tooth oriented in such a way that all objects as a whole are lined up to a user defined ideal arrangement. The template allows direct bonding of brackets and can be fabricated according to a simplified process, which is also disclosed herein. The process includes digitizing only some of the patient's teeth and/or simplifying the anatomical features of at least some of the patient's teeth; adding virtual objects to predetermined locations on the digitized teeth; and fabricating the dental template to locate the object on the patient's teeth. The dental template is designed to locate each object at a predetermined inclination or a predetermined angulation on the patient's tooth. The template can be used for etching or for positioning brackets on teeth. The skilled artisan will understand that the elements of the template and/or concepts of the fabrication methods described herein can be mixed and matched. For example, a template may be created using some steps from one method and other steps from one or more other methods.

The template is formed of a polymeric shell having a cavity shaped to fit over a patient's teeth and has openings that allow standardized brackets to be accurately positioned on teeth regardless of tooth surface variations from the norm for which the bracket base designed. The treatment can be done virtually and the placement of the brackets can be done using a template device that is a removable guide. This device allows precise placement of the bracket and enables bracket placement onto specific teeth independent of overall arch geometry. The template makes it easier for a less well-trained or an untrained person to bond a bracket. The system minimizes variations in the perception of distance and angles. The template allows precise control of the placement of the bracket. Since bracket placement is one of the critical variables to successful treatment, the template improves treatment precision from patient to patient and from tooth to tooth.

Figure 1:
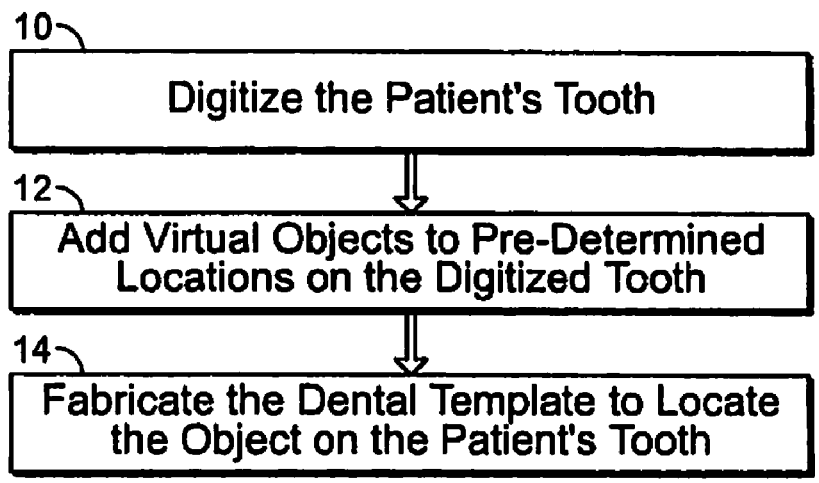
FIG. 1 shows an exemplary process for fabricating a dental template for positioning an orthodontic object on a patient's tooth.

FIG. 1 shows an exemplary process of fabricating a dental template for positioning an object on a patient's tooth. First, the process digitizes the patient's tooth (10). Next, virtual objects are added to pre-determined locations on the digitized tooth (12). Finally, the process fabricates the dental template to locate the object on the patient's tooth (14). One detailed implementation of the method of FIG. 1 is described with reference to FIGS. 3A-3E below.

Figure 2A:
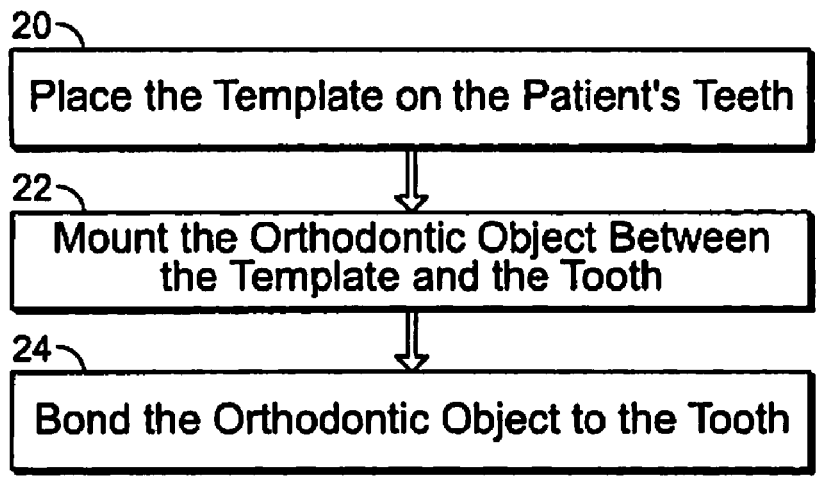
FIG. 2A shows an exemplary process for placing an orthodontic object on a patient's tooth.

FIG. 2A shows an exemplary process for placing an orthodontic object on a patient's tooth. The process uses the template fabricated in the process of FIG. 1. The process includes placing the template on the patient's teeth (20); mounting the orthodontic object between the template and the tooth (22); and bonding the orthodontic object to the tooth (24). In the bonding operation, chemical curing or light curing adhesives can be used. In chemical curing, separately supplied curing components are mixed together and a small quantity of the mixture is placed on the back of the bracket prior to placing the bracket on the tooth. Light-curable adhesives include a photo-initiator that initiates the curing reaction once the adhesive is exposed to a sufficient amount of light. A common method of using light-curable adhesives for direct bonding includes the steps of placing a small quantity of the adhesive on the base of the bracket and then placing the bracket on the patient's tooth. The practitioner then shifts the bracket on the tooth as may be needed. Once the bracket is in its intended location, light from a dental curing unit is directed toward the adhesive for a time period sufficient to satisfactorily cure the adhesive.

Figure 2B:
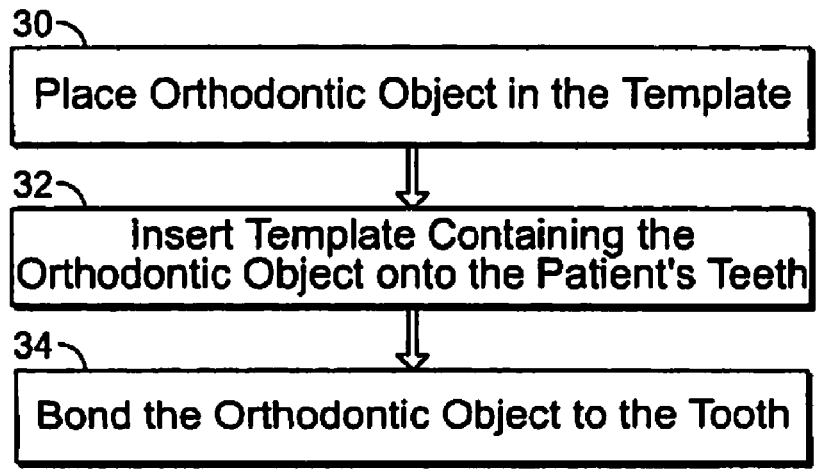
FIG. 2B shows another process for placing an orthodontic object on a patient's tooth.

FIG. 2B shows a second process of placing the orthodontic object on a patient's tooth. In this process, the orthodontic object is placed in the template (30). Next, the process includes inserting the template containing the orthodontic object onto the patient's teeth (32). Finally, the process includes bonding the orthodontic object to the tooth (34).

Figure 3A:
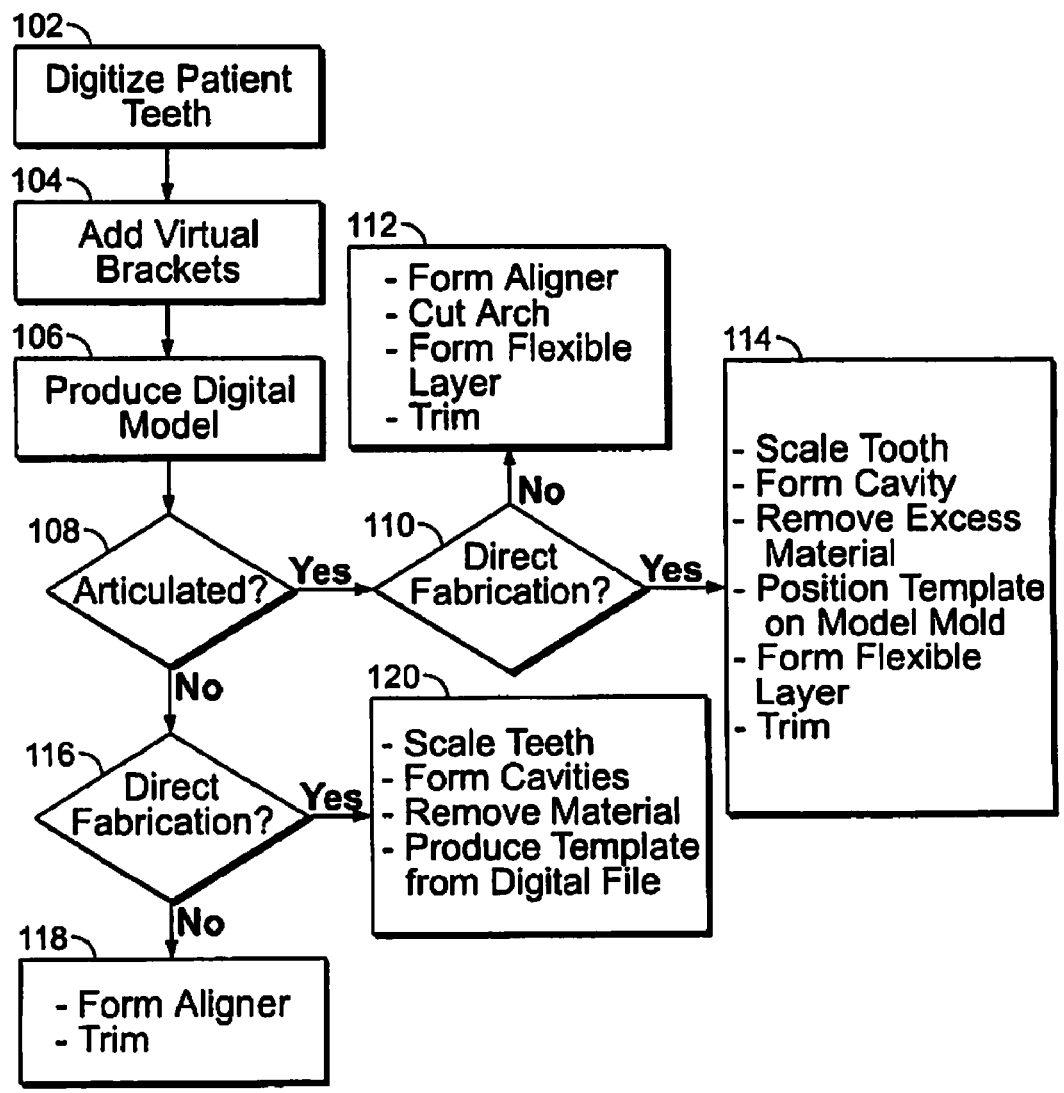
FIG. 3A illustrates an exemplary process for fabricating the dental template

FIG. 3A illustrates an exemplary process for fabricating the dental template. First, a digital model of a patient's teeth is obtained (102). The digital model can be obtained in a variety of ways. For example, the patient's teeth, or models thereof or impressions may be scanned or imaged using well-known technology, such as two or, three dimensional X-rays, computer-aided tomographic images or data sets, magnetic resonance images, etc. There are a variety of range acquisition systems, generally categorized by whether the process of acquisition requires contact with the three dimensional object (e.g., tooth) to be imaged. A contact-type range acquisition system uses a probe having multiple degrees of translational and/or rotational freedom. By recording the physical displacement of the probe as it is drawn across the sample surface of the object, a computer-readable representation of the sample object is made. A non-contact type range acquisition device can be either a reflective-type or transmissive-type system. There are a variety of reflective systems in use. Some of these reflective systems use non-optical incident energy sources, such as microwave radar or sonar. Others use optical energy. The non-contact type systems working by reflected optical energy further contain special instrumentation configured to permit certain measuring techniques to be performed (e.g., imaging radar, triangulation, and interferometry).

According to one embodiment, a digital model of only certain of the patient's teeth is obtained. For example, at least three teeth are digitized using one of the digitizing or scanning methods described above. According to an embodiment, four teeth are digitized for each of the upper (maxillary) and lower (mandibular) templates. In this embodiment, the four teeth for each of the upper and lower templates include the two central incisors and the two rearmost molars. The skilled artisan will understand that these four teeth can provide stability for positioning the template on a patient's teeth. In an alternative embodiment, three teeth for each of the upper and lower templates can be digitized: one of the central incisors and two mirror-image molars. According to another embodiment, all of the patient's teeth are digitized and a simplified digital model is later created, as discussed in more detail below.

Next, virtual brackets are selected and added (104) to the digital model of the patient's teeth. The virtual brackets are three-dimensional (3D) virtual models of physical brackets. The 3D model may be a computer aided design (CAD) model or may be scanned using scanners, as described above. The virtual brackets may be positioned on a digitized tooth using a computer or workstation having a suitable graphical user interface (GUI) and software appropriate for viewing and modifying the images. The above-described component identification and component manipulation software is designed to operate at sophistication commensurate with the operator's training level. For example, the component manipulation software can assist a computer operator, lacking orthodontic training, by providing feedback regarding permissible and forbidden manipulations on the teeth. On the other hand, an orthodontist, having greater skill in intra-oral physiology and teeth-moving dynamics, can simply use the component identification and manipulation software as a tool and disable or otherwise ignore the device.

While the methods described herein may rely on computer manipulation of digital data, the dental template or appliance may be produced by non-computer-aided techniques. For example, plaster casts, obtained as described above, may be cut using knives, saws, or other cutting tools in order to permit repositioning of individual teeth within the casting. The disconnected teeth may then be held in place by soft wax or other malleable material, and a plurality of intermediate tooth arrangements can then be prepared using such a modified plaster casting of the patient's teeth. The different arrangements can be used to prepare the template using pressure and vacuum molding techniques. While such manual creation of the appliance systems will generally be less preferred, appliance systems so produced will come within the scope of the present invention.

Using the CAD workstation, a combined digital model of the virtual brackets and the teeth can be produced (106). In one implementation, one of the two following template embodiments can be selected: Direct-Unified and Indirect-Unified, as discussed in more detail with reference to FIG. 3B.

Once the template has been fabricated, according to one embodiment, the template is set over the model of the patient's dental arches or otherwise positions the template in the approximate locations of their respective teeth. A thermo-formed cast, or otherwise formed layer of flexible material, is deposited on the bodies of the templates and makes relatively durable contact with the bodies of the templates. This method may be performed either in a factory or in an orthodontist's office.

The system can produce both the template bodies and the inter-tooth position(s) at the same time and subsequently alters the stiffness of the various parts. One way of achieving this would be to produce the entire arch with a 3D printer, mask the tooth bodies from the inter-tooth portions, and invest the tooth bodies with a rigidifying agent and the inter-tooth portions with an agent to create flexibility.

As shown in FIG. 3A, from 110, if a directly formed template is produced, the process proceeds to 114, where each tooth is scaled; a cavity is then formed to enclose the tooth when the dental template or appliance is inserted over the patient's teeth. Next, excess material or unnecessary structures (e.g., anatomies of certain teeth, occlusal portions, and gingival portions) are removed from the digital model. The digital model is produced as a physical model. A flexible, pliable layer is formed and the resulting combination is trimmed to allow proper fit and function.

From 108, if a template of a whole arch (not articulated) is to be produced, the process proceeds to 116. In the case of an indirectly-produced template, the process forms an Aligner and excess material is removed (118).

In the case of a directly formed whole arch template, the process proceeds from 116 to 120 where the entire arch is scaled; cavities are then formed to enclose the arch when the dental template or appliance is inserted over the patient's teeth. Next, excess material or unnecessary structures (e.g., certain teeth, occlusal portions, gingival portions) are removed from the digital model. The digital model is produced as a physical model. A flexible, pliable layer is formed and the resulting combination is trimmed to allow proper fit and function.

Figure 3B:
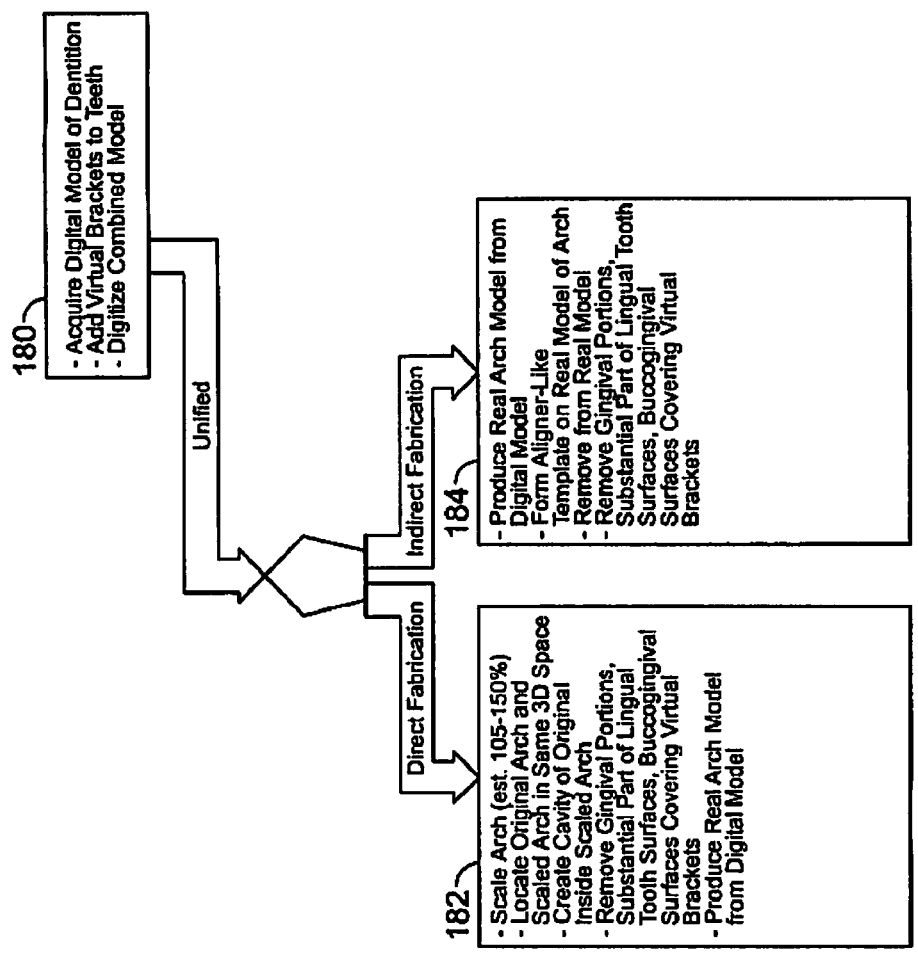
FIG. 3B shows a process for providing four possible templates.

FIG. 3B shows a process for providing two possible templates. First, the process acquires a digital model of dentition, adds virtual brackets to the teeth, and creates a combined model (180) including the dentition and the virtual brackets. Next, one of two template options can be selected.

Figure 3C:
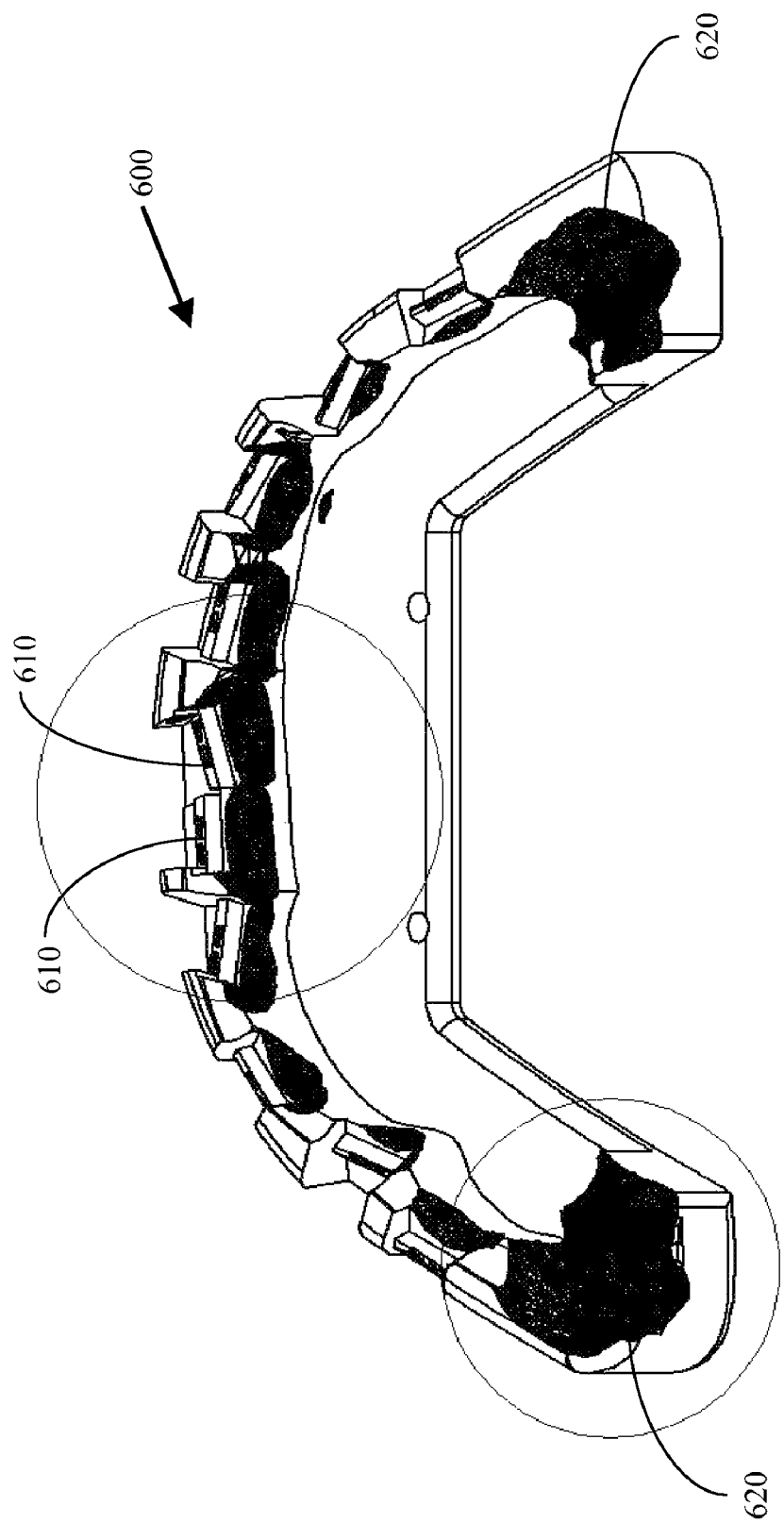
FIG. 3C illustrates an embodiment of a simplified template having only certain reproduced features of a patient's teeth.
Figure 3D:
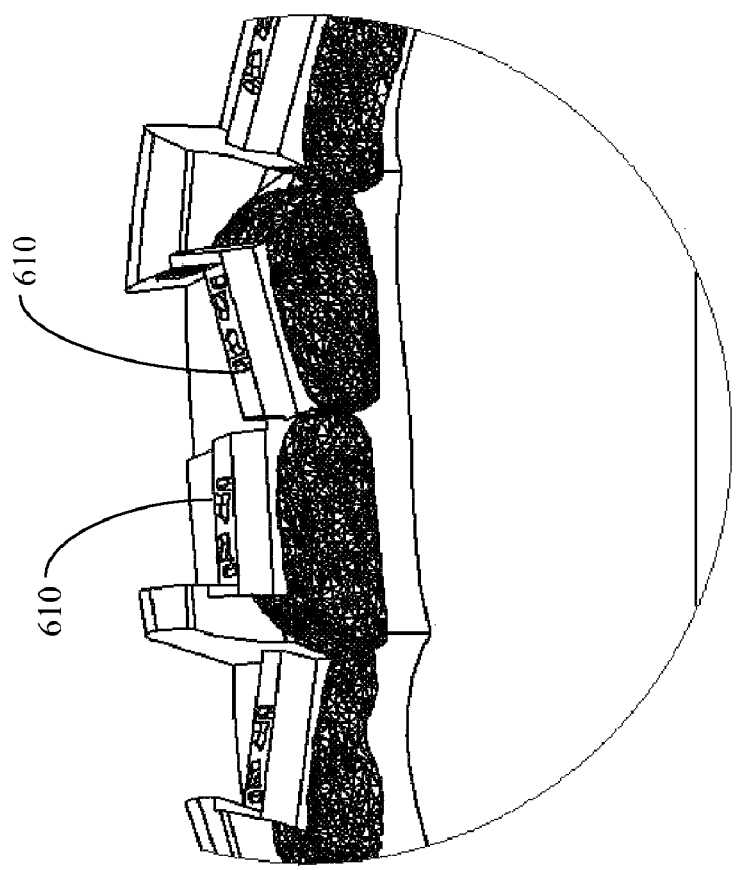
FIG. 3D shows in greater detail the area in circle A of FIG. 3C.
Figure 3E:
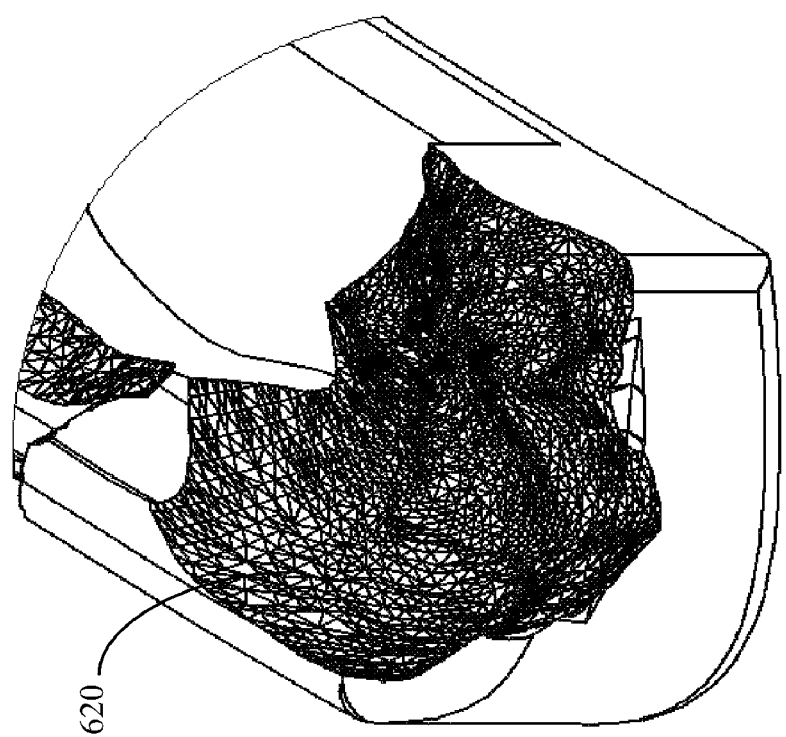
FIG. 3E shows in greater detail the area in circle B of FIG. 3C.

The first option is a unified (or single piece) direct fabrication option where the process scales the patient's dental arch (about 105-150%), locates the original arch and scaled arch in the same 3-D space, creates a cavity of the original inside the scaled arch, removes gingival portions, tooth geometries of the occlusal portions of most teeth except for the positioning teeth, substantial portion of lingual tooth surfaces, substantial portion of the buccal surfaces, and buccogingival surfaces covering virtual brackets, and produces a real arch model from the digital model (182). For example, the occlusal portions of most of the teeth (i.e., teeth that are not used as positioning teeth) in the real arch model (and also the simplified combined digital model) may be substantially planar. According to an embodiment, not only are the tooth geometry features significantly reduced and simplified as noted above, but also the number of teeth having features reproduced; for example, a great deal of the tooth geometries are removed from all teeth except for four or fewer teeth used as positioning teeth. In one exemplary embodiment of a template 600 illustrated in FIGS. 3C-3E, only certain features are reproduced for four positioning teeth in each of the upper (maxillary) and lower (mandibular) templates: the two central incisors 610 (e.g., teeth #24 and #25 in the lower template) and the two rearmost molars 620 (e.g., teeth #19 and #30 in the lower template). For example, the occlusal surfaces are reproduced only for these four teeth 610, 620; the remaining teeth have substantially planar occlusal surfaces because they are simplified. The skilled artisan will appreciate that the four teeth 610, 620 and their reproduced features are useful in positioning the template 600 on the patient's dental arch, and that the simplified real arch model may be fabricated more quickly because it has fewer reproduced features of the patient's teeth. Such a simplified model and template 600 made using such a simplified model also requires less material. According to the embodiment of FIGS. 3C-3E, the template 600 is positioned using only the incisal surfaces of the central incisors 610 and the occlusal surfaces of the rearmost molars 620, rather than using all teeth. As shown in FIGS. 3C-3E, the incisal and occlusal surfaces are reproduced only in the central incisors 610 and rearmost molars 620. As shown in FIG. 3C, the occlusal surfaces of the remaining teeth in the template 600 are substantially planar, as they have been simplified and those of skill in the art will understand that adequate clearance in the upper and lower templates should be provided to limit occlusal surface contact for these other simplified teeth. It will be understood that the reproduced occlusal features of the central incisors 610 and the rearmost molars 620 are used to locate the template 600 along the z-axis and the template walls contacting each tooth's buccal surface are used to locate and secure the template 600 in the x and y direction. The skilled artisan will appreciate that only the occlusal surfaces of the patient's teeth having reproduced occlusal features on the template 600 contact the template 600 when the template is positioned on the patient's teeth. In alternative embodiments, other teeth can be selected for positioning the template. For example, for the upper template, teeth #2, #8, #9, and #15 may be selected and teeth #18, #24, #25, and #31 may be selected for the lower template. Also as noted above, three teeth may be selected: preferably, one of the central incisors and two contra lateral molars. The digital model is then converted to a physical model, likely through the use of a rapid prototyping method (e.g., Fused Deposition Modeling, 3-D Printing, and stereolithography).

In the second option (unified indirect fabrication), the process produces a real model (e.g., mold) of the arch from a simplified digital model and forms a removable appliance (aligner) template on the real model of the arch. The real model can be fabricated using rapid prototyping methods. The skilled artisan will understand that the digital model is simplified by removing occlusal portions and buccal portions such that they are substantially planar in most of the teeth. The template is removed from the real model, and the process continues by removing gingival portions, substantial portion of lingual tooth surfaces, and buccogingival surfaces covering virtual brackets from the template (184). According to an embodiment, not only are the tooth geometry features significantly reduced and simplified, as noted above, but also the number of teeth having features reproduced on the real model of the arch; for example, the entire tooth geometries are removed from all teeth except for four or fewer teeth. In one embodiment, only certain features of four teeth remain for each of the upper (maxillary) and lower (mandibular) templates: the two central incisors and the two rearmost molars. The skilled artisan will appreciate that, as discussed above, these teeth and their reproduced features are useful in positioning the template on the patient's dental arch, and that the simplified real arch model may be fabricated more quickly because it has fewer features of the patient's teeth. The digital model is then converted to a physical model, likely through the use of a rapid prototyping method (e.g., Fused Deposition Modeling, 3-D Printing, and stereolithography).

In one embodiment, the template 600 is made from a thicker material (for example, at least 0.03 inch) to provide the user with more guidance in the depth direction. The thicker material for the template 600 is preferably in a range of about 0.02-0.06 inch, more preferably in a range of about 0.03-0.05 inch, and even more preferably about 0.04 inch. Furthermore, the thicker template allows easier positioning of the bracket to the tooth as there is more bracket surface area supported by the material. The template 600 may be made from materials that contain physical property switches for ease of removal. These switches might include temperature responsive, pH responsive, moisture responsive, or a multi-layer system wherein the layers have varying physical properties. More information on the fabrication of a dental template or appliance is disclosed in U.S. patent application Ser. No. 10/794,324, entitled "Systems and Methods for Fabricating a Dental Template With a 3-D Object Placement," filed Mar. 4, 2004, the entire disclosure of which is hereby incorporated herein by reference.

Another embodiment of the template can be used for etching bonding chemicals on the patient's teeth. An etching template allows the practitioner to precisely etch the areas of the teeth on which the bracket will be placed. The etching template directs the user to predetermined locations on the teeth surface that need to be bonded. The etching template can be either a windowed template or a concave surfaced template where bonding gel is loaded or pre-loaded into the concavity. In some embodiments, cut-outs or windows of the template bound the regions to be etched to minimize teeth sensitivity to etching or unwanted enamel removal. In another embodiment of the etching template, the cut-outs or windows are not formed; instead, those areas are formed as concavities facing the tooth surfaces. The concavities can contain an etching compound, which can be exposed or activated prior to setting the template on the teeth.

Various alternatives, modifications, and equivalents may be used in lieu of the above components. Additionally, the techniques described herein may be implemented in hardware or software, or in a combination of the two. The techniques may be implemented in computer programs executing on programmable computers that each includes a processor, a storage medium readable by the processor (including volatile and nonvolatile memory and/or storage elements), and suitable input and output devices. Each program can be implemented in a high level procedural or object-oriented programming language to operate in conjunction with a computer system. However, the programs can be implemented in assembly or machine language, if desired. The language may also be a compiled or interpreted language. Each such computer program can be stored on a storage medium or device (e.g., CD-ROM, hard disk, magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium causes a computer to operate in a specific and predefined manner. Further, while the invention has been shown and described with reference t an embodiment thereof, those skilled in the art will understand that the above and other changes in form and detail may be made without departing from the spirit and scope of the following claims.

What is claimed is:

1. A method of fabricating a dental template configured to position an object on teeth of a patient, comprising:
    creating a digital model of the teeth of the patient;
    creating a template model comprising an arch having a first portion and a second portion, the first portion comprising at least one tooth receiving cavity having geometries corresponding to the shape of the patient's tooth in the digital model, and the second portion comprising a substantially planar occlusal portion spanning multiple teeth of a patient's arch, the substantially planar occlusal portion omitting at least one occlusal feature of each of the spanned teeth; and
    fabricating the dental template using the template model.

2. The method of claim 1, wherein the template model comprises no more than four positioning teeth in the first portion, the positioning teeth having reproduced features of occlusal surfaces of corresponding positioning teeth of the patient.

3. The method of claim 2, wherein the corresponding positioning teeth of the patient include at least one central incisor and two molars.

4. The method of claim 1, wherein the template model is created using a rapid prototyping technology.

5. The method of claim 4, wherein the rapid prototyping technology is fused deposition modeling.

6. The method of claim 1, further comprising simplifying the digital model before creating the template model, wherein simplifying comprises removing certain geometry features of some of the teeth of the patient.

7. The method of claim 6, wherein simplifying comprises removing occlusal features of some of the teeth of the patient.

8. The method of claim 1, further comprising positioning the object on the template model.

9. A method of fabricating a dental template configured to position an object on a patient's teeth, the method comprising: creating a digital model of the teeth of the patient; creating a template model comprising an arch having a first portion and a second portion, the first portion comprising teeth receiving cavities having geometries corresponding to the shape of the patient's teeth in the digital model, the teeth receiving cavities configured to be positioned on the patient's teeth using incisal or occlusal surfaces of four or fewer teeth, and the second portion comprising substantially planar occlusal portions spanning multiple teeth of a patient's arch, the substantially planar occlusal portions omitting at least one occlusal feature of the corresponding spanned teeth; and fabricating the dental template using the template model.

10. The method of claim 9, wherein the incisal or occlusal surfaces of the four or fewer teeth are the only incisal or occlusal surfaces on the dental template that contact incisal or occlusal surfaces of the patient's teeth when the dental template is positioned on the patient's teeth.

11. The method of claim 9, further comprising simplifying the digital model of the patient's teeth by reducing digitized features of the patient's teeth.

12. The method of claim 11, wherein reducing digitized features of the patient's teeth comprises replacing some digitized tooth surfaces with substantially planar surfaces.

13. The method of claim 11, wherein the template model is created using rapid prototyping technology.

14. The method of claim 9, wherein the template model comprises no more than four teeth having features corresponding to features of the patient's teeth.

* * * * *

UNITED STATES PATENT AND TRADEMARK OFFICE
CERTIFICATE OF CORRECTION

| | | |
|---|---|---|
| PATENT NO. | : 8,401,686 B2 | Page 1 of 1 |
| APPLICATION NO. | : 12/338307 | |
| DATED | : March 19, 2013 | |
| INVENTOR(S) | : Moss et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 377 days.

Signed and Sealed this
Second Day of December, 2014

Michelle K. Lee
*Deputy Director of the United States Patent and Trademark Office*